United States Patent [19]

Cobean

[11] 4,276,333
[45] Jun. 30, 1981

[54] APPARATUS AND METHOD FOR SOLVENT ADHESION OF COILED TUBING, AND PRODUCT PRODUCED THEREBY

[75] Inventor: Richard W. Cobean, Libertyville, Ill.
[73] Assignee: Baxter Travenol Laboratories, Inc., Deerfield, Ill.
[21] Appl. No.: 87,075
[22] Filed: Oct. 22, 1979
[51] Int. Cl.$^3$ .............................................. D02G 3/00
[52] U.S. Cl. ...................................... 428/36; 118/242; 118/321; 156/195; 156/291; 156/296; 156/305; 156/433; 156/443; 156/578; 428/114; 428/188; 428/294; 428/371
[58] Field of Search .................. 156/291, 184, 195, 305, 156/578, 296, 433, 443, 446; 118/321, 323, 240, 241, 242; 264/281; 346/116, 117 R, 140 R; 428/188, 371, 36, 114, 294

[56] References Cited

U.S. PATENT DOCUMENTS

| | | | |
|---|---|---|---|
| 2,397,743 | 4/1946 | Kaphan | 428/195 |
| 2,438,685 | 3/1948 | Stevens | 156/304.6 |
| 2,757,710 | 8/1956 | Schanz | 156/153 |
| 2,814,581 | 11/1957 | Flynn | 156/169 |
| 2,977,928 | 4/1961 | Knutsey | 118/323 X |
| 3,009,209 | 11/1961 | Weinbrenner | 264/54 |
| 3,312,579 | 4/1967 | Heifety | 156/305 |
| 3,479,986 | 11/1969 | Hoover | 156/578 X |
| 3,700,531 | 10/1972 | Schruff et al. | 156/575 |
| 3,821,047 | 6/1974 | Schruff et al. | 156/69 |
| 3,853,670 | 12/1974 | Cox et al. | 156/562 |
| 3,854,385 | 12/1974 | Wallin | 93/36 MM |

FOREIGN PATENT DOCUMENTS 209568 7/1957 Australia ............................. 428/188

Primary Examiner—David A. Simmons
Attorney, Agent, or Firm—Paul C. Flattery; John A. Caruso; Q. Todd Dickinson

[57] ABSTRACT

Lengths of tubing, especially that type of tubing suitable for use in medical equipment and devices, are weakly bound into a coil shape in order to facilitate handling and storage thereof while at the same time placing the tubing into a form that will make the full length thereof readily available by merely applying a slight pulling force to the ends of the coiled tubing. The solvent is applied in a very narrow uninterrupted stream, which stream tracks along one or more locations on a length of tubing that has been wound around a mandrel, which stream is dispensed by a mechanism that simultaneously carries out such tracking in a manner that is synchronized automatically with the dispensing of the stream and without the need for separate control mechanisms with the result that the tracking and dispensing are carried out at substantially the same ratio, with the same general consistency or inconsistency of travel, to the extent that the amount of solvent dispensed per turn of the coil is inherently uniform.

21 Claims, 12 Drawing Figures

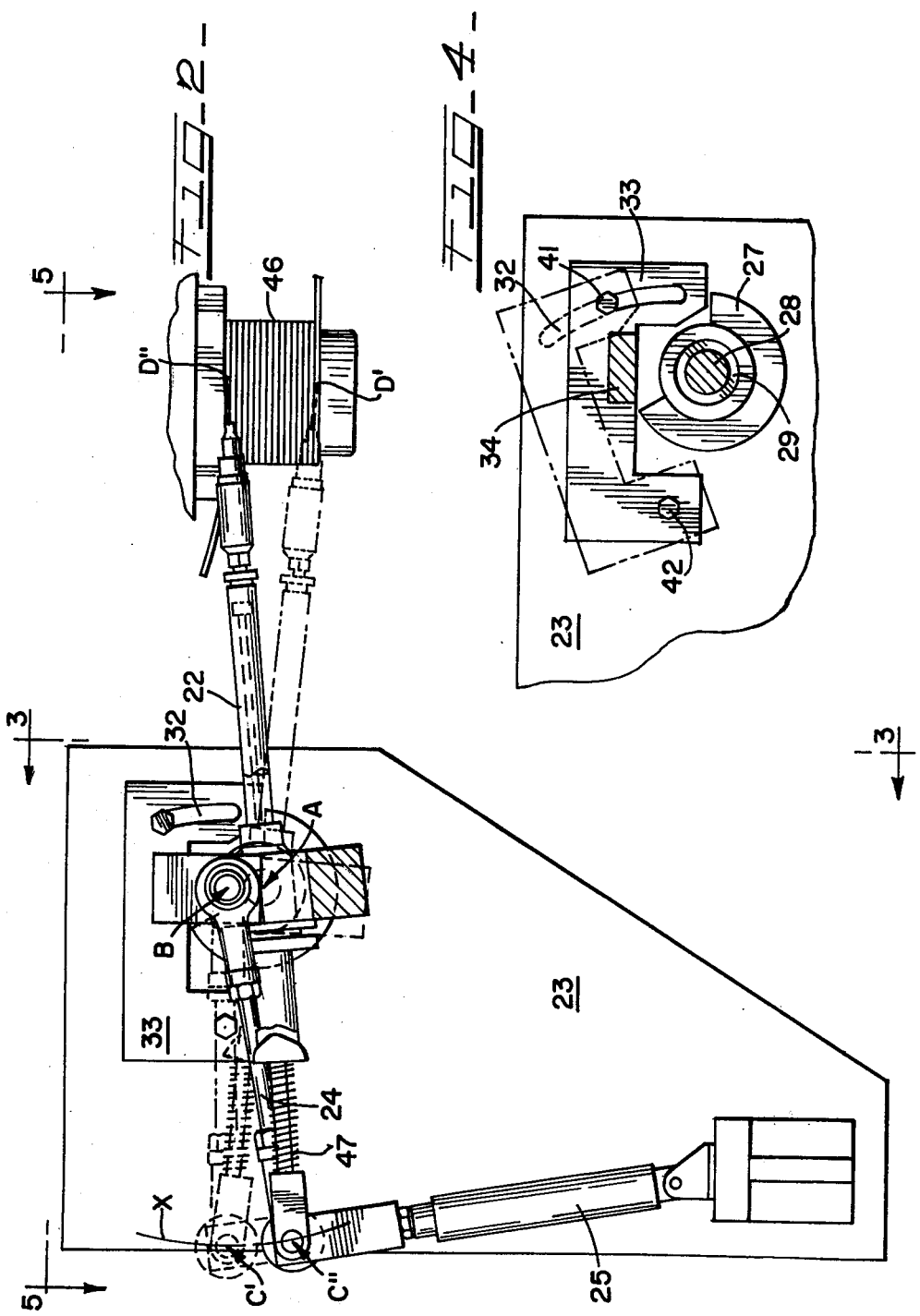

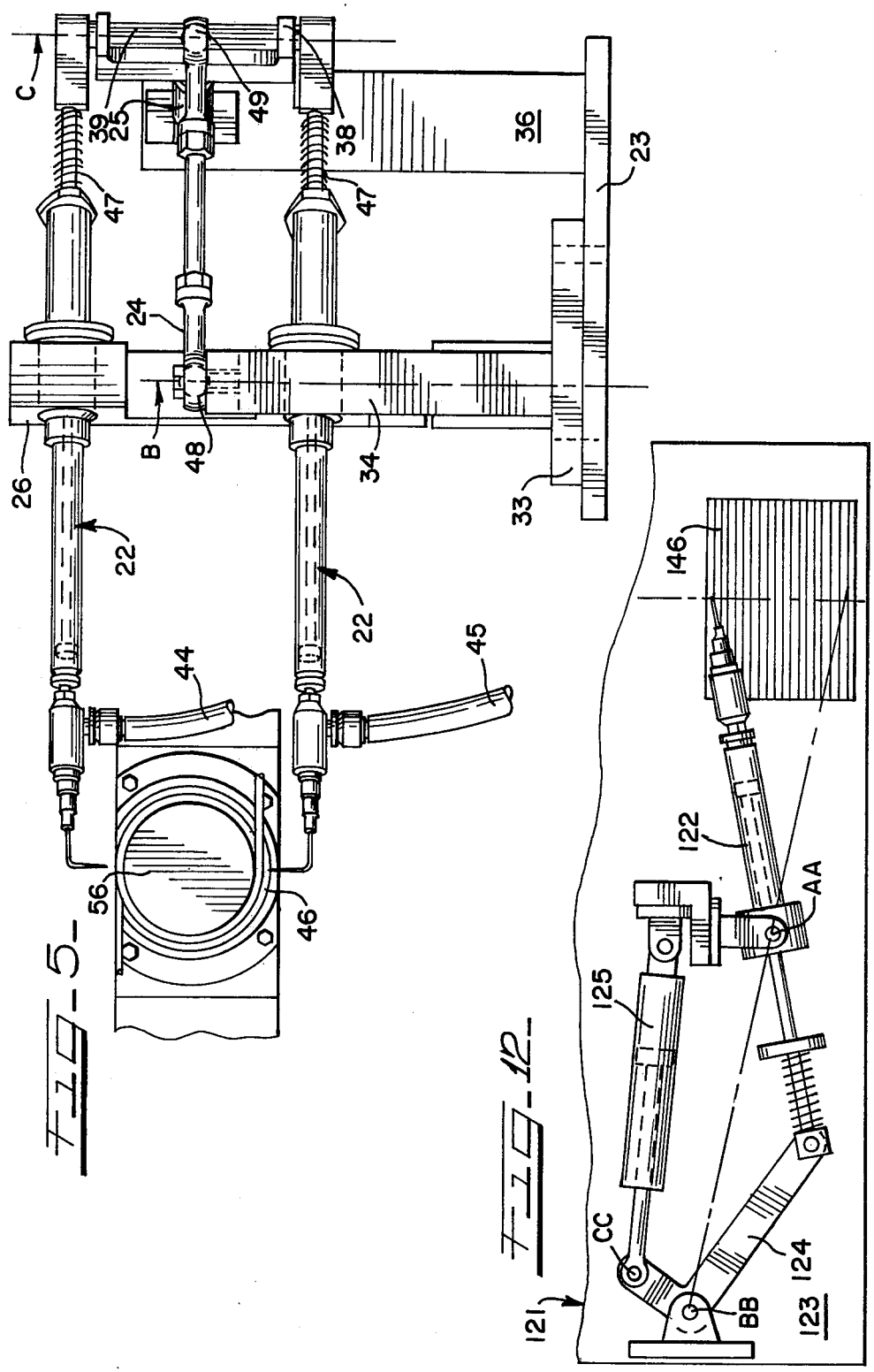

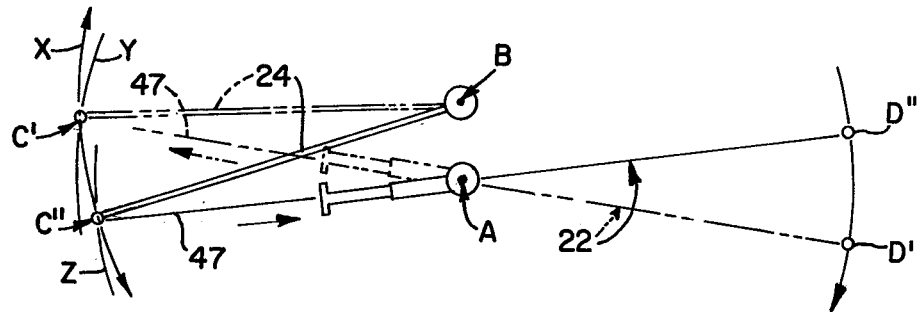
FIG_6_
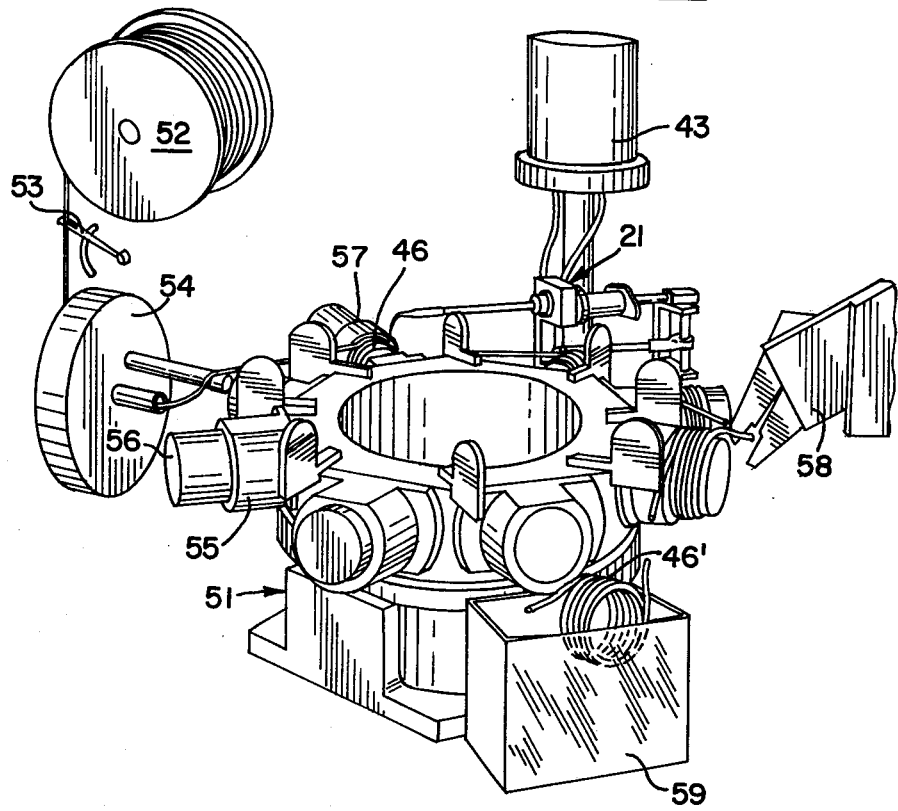
FIG_7_

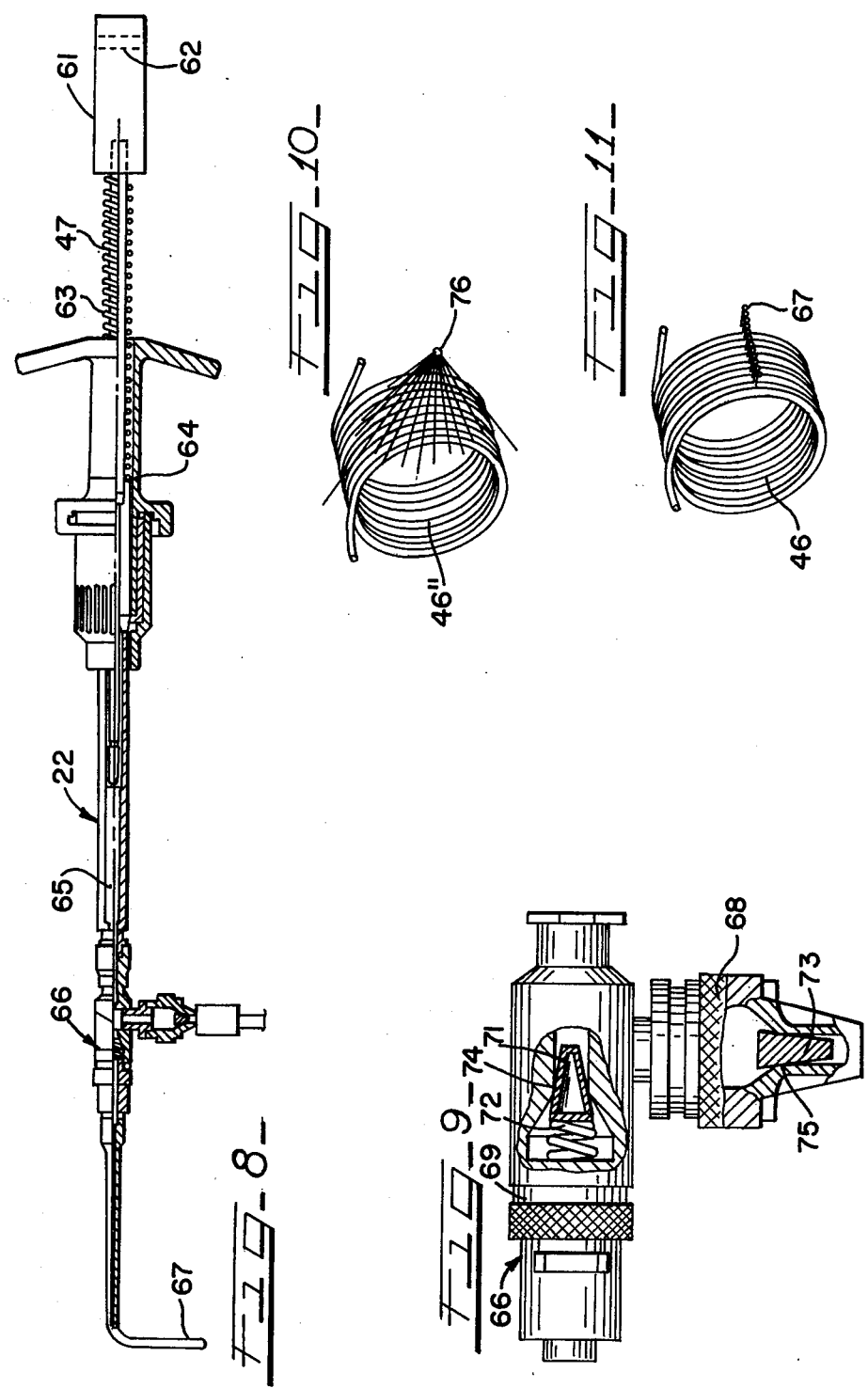

APPARATUS AND METHOD FOR SOLVENT ADHESION OF COILED TUBING, AND PRODUCT PRODUCED THEREBY

BACKGROUND AND DESCRIPTION OF THE INVENTION

This invention relates generally to preparing coils of tubing, the tubing coils being especially suitable for use in medical equipment and medical devices in which compactly stored, tangle-free tubing is often extremely important. Various aspects of the invention include a method and an apparatus having means for dispensing a substantially uninterrupted stream of solvent through an extremely narrow orifice while automatically simultaneously tracking the orifice through a narrow band generally along tubing that has been coiled together in order to dissolve tubing surface and adhere such dissolved surfaces together where they are in contact with each other, another aspect of the invention being the weakly bonded tubing coil prepared in accordance therewith.

It has been known that, by coiling tubing into a helix and lightly adhereing together adjacent coils or turns, a portion of tubing several feet in length can be better handled during assembly of fittings to either end of the tubing, while packaging same into a compact unit, and when handling up to and at the point of use, such as in a hospital when the tubes are part of medical equipment or devices, for example, pressure monitoring or heparin infusion tubes for kidney dialysis machines, in blood bags for collecting and dispensing blood, and units for dispensing intravenous fluids, plasma, gases, or the like. When such a coil is to be put into use, it is removed from its package, and its ends are pulled apart so that the tubing is returned to a relatively straight length, free of knots, kinks and tangles.

Heretofore, commercial scale operations for coiling relatively stretchable tubing of the type typically used in medical equipment and devices, especially disposable medical tubing, have not been fully automated to the extent that the coil itself is automatically wound, a solvent is uniformly and automatically applied to the coil by mechanically synchronized tracking and dispensing, after which the solvent rapidly dries to adhere the individual turns together.

Equipment for automatically winding coils has long been in use, especially for winding coils onto bobbins or spools on which the wound coil is to be stored. Modification of such equipment makes possible the preparation of free-standing coils by winding on a mandrel, adhering adjacent turns together, drying as necessary, and removing the mandrel in order to prepare a coil that does not have a bobbin or spool therewithin.

Typically, such equipment will apply the solvent by spraying. Spraying often includes the incorporation of air or other gas into a liquid solvent so as to propel the solvent onto the coil, usually causing significant splashing and the application of much more solvent than is actually needed to adhere the coil together, thereby wasting solvent and substantially increasing the drying time needed, all of which are inefficient and costly, such being especially critical for preparing a relatively inexpensive item such as a length of tubing for which it is desired to minimize processing costs.

By the present invention, spraying of solvent is eliminated, the solvent being applied by dispensing in an extremely narrow stream near the surface of the coil by means of a narrow orifice such as that provided by a hypodermic needle, syringe dispenser, or the like, while simultaneously tracking that narrow stream in a narrow path generally parallel to the height of the coil. Then, capillary action spreads the solvent between the closely adjacent turns of tubing, whereby the very narrow path widens, but only after actual application of the coil, in order to form a broad adhesion band which extends on either side of the narrow path that was dispensed and tracked. The stream, which is entirely liquid solvent, is extremely narrow and of an amount having substantially no excess over that needed to just wet each turn at a location approximating a locus of points, this minimal amount encouraging the capillary action for spreading the solvent, capillary action conditions being enhanced when only minute amounts of liquid are confined within narrow pathways, such as those provided by the adjacent coils.

The unbroken stream of solvent according to this invention is applied substantially uniformly and without the use of any propelling gases, thereby substantially eliminating splashing and application of excess solvent to thereby minimize the amount of solvent needed, reduce the drying time significantly, and minimize the volume of exhaust or ventilation air needed in order to safely dispose of any solvent that volatilized into the surrounding air during the drying stage. Additionally, spraying the solvent with propelling and atomizing gases such as air evaporates some of the solvent before it reaches the coiled tubing, and the solvent reaching the tubing is a mist of droplets so small that much of the solvent evaporates before reaching the contact line between the adjacent coils, the intended point of application, thereby further wasting solvent.

It is accordingly a general object of the present invention to provide an improved method and apparatus for producing coils of tubing, and the tubing coils produced thereby.

Another object of this invention is an improved apparatus and method including a single mechanical structure for both dispensing solvent and traversing a solvent delivery path to the extent that the dispensing and traversing are inherently synchronized so that even if the dispensing rate varies during a given cycle or from unit to unit or over long periods of time, the amount of solvent delivered to each turn or coiled space is inherently uniform.

Another object of the present invention is an improved method, apparatus and product in which capillary action, rather than spraying, distributes solvent along the areas of contact between adjacent turns of tubing coil in order to reduce the amount of solvent needed to produce an adhered band in the coil produced.

Another object of this invention is an improved method, apparatus and product which includes squirting a very narrow path or locus of solvent along a coil by passing the solvent through a narrow orifice as it tracks along a wound coil.

Another object of this invention is an improved method, apparatus and product including use of a syringe that is tracked along a wound coil by the same mechanism that depresses the plunger of the syringe for dispensing solvent therefrom.

Another object of the present invention is an extremely efficient means and method for producing extremely efficiently even on a commercial scale, wound tubing coils having its turns weakly adhered together, by using extremely small quantities of uniformly applied solvent.

These and other objects of this invention will become apparent from the following detailed description, taken in conjunction with the accompanying drawings, wherein:

FIG. 2 is a top plan view illustrating the traversing and dispensing mechanism in further detail;

FIG. 4 is a sectional view along the line 4—4 of FIG. 3;

FIG. 5 is a view along the line 5—5 of FIG. 2;

FIG. 6 is a schematic view of the simultaneous and synchronized traversing and dispensing mechanism in accordance with this invention;

FIG. 7 is a perspective view of a multi-stationed coil winding apparatus including the preferred tracking and dispensing apparatus illustrated in FIG. 1.

FIG. 8 is a detail view, partially in section, of the syringe portion of the preferred tracking and dispensing means;

FIG. 9 is an enlarged view, partially in section, of the two-way check valve mechanism that is included in the syringe of FIG. 8:

FIG. 10 is an illustrative perspective view of a tubing coil, depicting spraying of solvent not in accordance with this invention;

FIG. 11 is an illustrative perspective view of a tubing coil, depicting the tracking and dispensing path in accordance with this invention; and FIG. 12 is a top plan view of an alternative embodiment of the tracking and dispensing mechanism of this invention.

Figure 1:
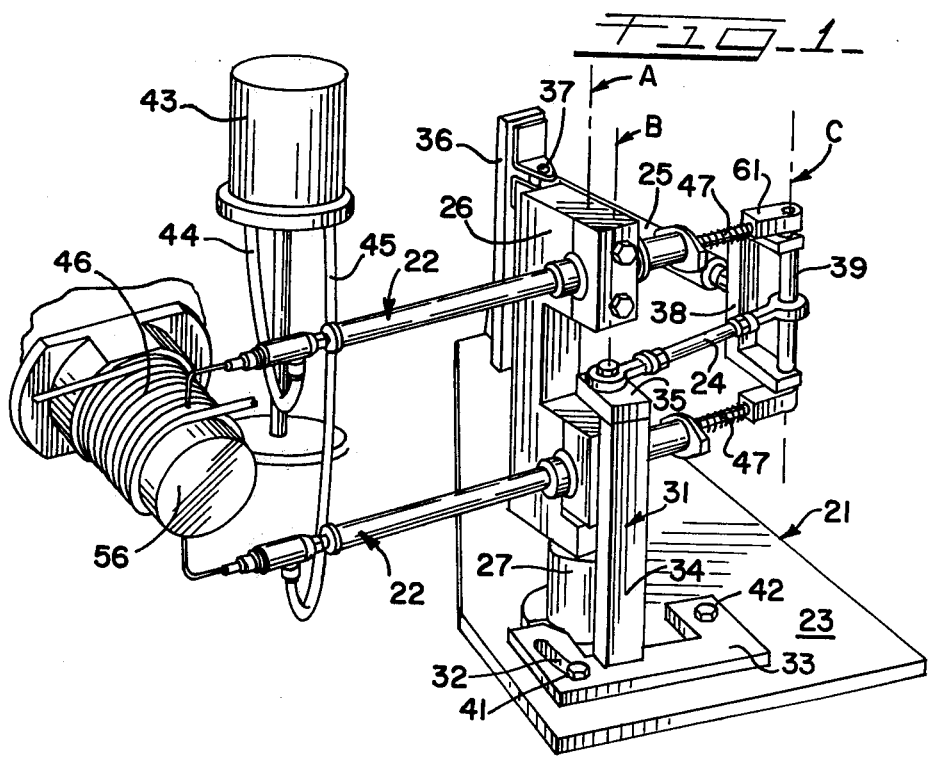
FIG. 1 is a perspective view of the preferred dispensing and traversing mechanism of this invention.

The preferred tracking and dispensing mechanism, which is generally indicated by reference numeral 21 in FIG. 1, includes one or more dispensing means 22 pivotally mounted to a base 23 along an axis "A"; a rigid arm 24 that is pivotally mounted to the base 23 along an axis "B" which is offset with respect to axis A, with each of the opposite ends of the dispensing means 22 and the rigid arm 24 being pivotally mounted to each other along an axis "C"; and means 25 effecting rotation of the dispensing means 22 about axes A and C and for rotating the rigid arm 24 about axes B and C. Preferably, axis C is not a stationary axis, but it is movable in response to movement provided by the rotation effecting means 25, as constrained by the rigid arm 24. Movement of axis C tracks dispensing means 22 while simultaneously operating the means 22 in order to dispense liquid therefrom.

In the preferred embodiment illustrated in FIGS. 1 through 5, rotation means 25 is a telescoping arm mounted onto the base 23 and pivotally mounted along axis C to both the opposite end of the rigid arm 24 and the opposite end of the dispensing means 22, which is a dispensing syringe. Rotation means 25 can alternatively take the form of any device or structure that will provide the required rotation about the axes, such as an electric motor mounted onto a shaft being along any of the axes.

Details of the tracking and dispensing mechanism 21 of the preferred embodiment include a dispenser support block 26 pivotally mounted onto a bearing housing 27, the pivotal mounting along axis A being onto a pivot shaft 28 within bearings 29. One end of the rigid arm 24, that end mounted along axis B, is pivotally mounted onto a pivot support arm, generally designated 31 that is rigidly mounted to base 23.

Figure 3:
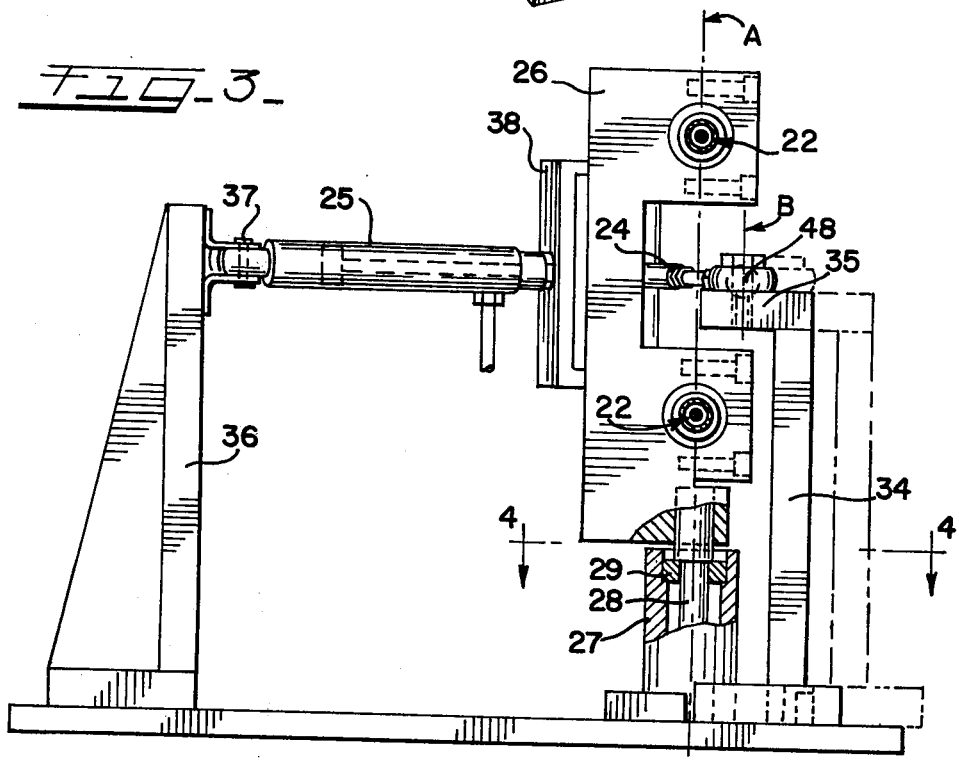
FIG. 3 is an elevation view, partially broken away, along the line 3—3 of FIG. 2.

It is preferred that the mounting of the rigid support arm 31 onto the base 23 is adjustable in order to vary the distance between axis A and axis B, this feature typically being provided by a slot 32 within a mounting shoulder bracket 33 of pivot support arm 31. Adjustment available by means of the slot 32 is illustrated in FIGS. 3 and 4 in which the maximum distance being adjusted by moving mounting shoulder bracket 33 along its slot 32 and securing the desired location by tightening adjustment bolt 41 and securement bolt 42.

To provide adequate clearance, the pivot support arm 31 will typically be L-shaped to include a longitudinal arm 34 and a transverse member 35 onto which the one end of the rigid arm is mounted.

When the rotation means 25 is a telescoping arm, typically one that includes an air activated piston, it is conveniently mounted at one end thereof by a pivot pin 36 in a support bracket 37 that is secured to the base 23, with the opposite end of the telescoping arm 25 being rigidly secured to a yoke member 38. A movable pivot shaft 39 pivotally joins the yoke member 38, the opposite end of the rigid arm 24, and the opposite end of the dispensing means or syringe 22.

As can be seen in FIG. 5, the pivotal connection of both the one end and the opposite end of the rigid arm 24 preferably includes a ball joint mechanism 48, 49 in order that the rigid arm 24 will be free to rotate slightly along its own axis in order to lessen any chance of binding due to slight nonuniformities in the dispensing syringes themselves or in their operation, either of which could lead to rotational misalignment of the rigid arm 24, in order to thereby render the rigid arm, although free of slack in its length, tolerant of misalignment in other directions. Preferably the rigid arm 24 is in the nature of a telescoping strut having a preload pressure that is well above the forces encountered during operation of the tracking and dispensing mechanism 21 and that is still low enough to be easily overcome by human hands. Such a preload pressure telescoping rigid arm 24 ensures that rigid arm 24 remains at a consistent length during operation while permitting an operator to overcome the preload pressure for conveniently depressing the syringes, even while they are mounted within the dispenser support block 26, in order to "bleed" the syringe dispenser 22 free of any entrapped fluids other than the liquid to be dispensed.

Liquid is supplied to the dispensing syringe 22 from a reservoir 43 through tubing 44, 45, with the reservoir 43 preferably being at a height somewhat above that of the dispensing syringe 22 in order to provide a slight gravity feed. A coil of tubing 46 is positioned within the tracking path of the dispensing syringe 22, which tracking path can extend over the initial, typically the outside, edge of the coil 46, preferably stopping at or just before the final, typically the inside, turn of the coil.

Operation of the preferred tracking and dispensing mechanism 21 is illustrated by phantom lines in FIG. 2 and by schematic illustration in FIG. 6. By counterclockwise rotation brought about by rotation means, which is accomplished in the preferred embodiment by retraction of the telescoping arm 25, the axis C moves from location C' to location C'', and clockwise rotation, by extension of the telescoping arm 25 of the preferred embodiment, brings about movement from location C'' to location C'. During such movement of the axis C, the one end of the rigid arm 24 rotates about the stationary axis A, and the rigid arm 24 does not change in length. Dispensing syringe 22 pivots about the stationary axis A, and the tracking function is accomplished as the dispensing end of the dispensing syringe 22 move from point D' to point D" as axis C moves from point C' to point C", and the dispensing end returns to its initial position by moving from point D" to D' as axis C moves from point C" to point C'.

The dispensing function which is synchronized and simultaneous with this tracking function takes place also as axis C moves from point C' to point C" along arc X, during which movement a plunger 47 of the dispensing syringe 22 is pushed into the syringe 22 in order to dispense therefrom the liquid therewithin. Such pushing of the plunger 47 is accomplished because rigid arm 24 remains at a uniform length as the axis C moves from point C' (which is the same distance from point B as is point C") and to point C" (which is closer to point A than is point C'). Inasmuch as point A and point B are offset from each other and the length BC' equals the length BC", the length AC' is greater than the length AC", illustrated in FIG. 6 as the distance between arc Y and arc Z, this difference in length being the distance that the plunger 47 is inserted into the dispensing syringe 22, which amount precisely determines the volume of liquid dispensed. Movement from point C' to point C" depresses the plunger 47 at a rate of depression, whether that rate be constant or variable, uniform or nonuniform, that corresponds directly to the tracking rate movement from point D' to point D", which tracking rate is thus identically constant or variable, uniform or nonuniform, with the result that the tracking and dispensing are at a ratio with each other that is substantially constant such that the quantity of liquid delivered to each turn of the coil of tubing 46 is inherently uniform for a given tubing diameter.

The tracking and dispensing mechanism of this invention is advantageously used in combination with a multi-station coil winding apparatus of the type illustrated in FIG. 7, generally referred to by reference numeral 51. The coil winding apparatus 51 includes a supply spool 52 having the tubing to be processed, the spool being associated with an unwinding spool mechanism 53 and a feed mechanism 54, which are of a structure generally known in the wire winding art. Apparatus 51 includes a plurality of stations 55 each having a retractable mandrel 56. After the tubing is wound into a coil 46 onto one of the mandrels 56, the coil 46 is preferably contacted by a pusher 57 which slides over the outside portion of the mandrel 56 for a distance or length that had been previously detemined to be adequate to place the individual turns of the coil of tubing 46 into adjacent contact with each other while avoiding deformation of the tubing coil 46.

Tracking and dispensing mechanism 221 dispenses and tracks along the coil of tubing 46, which coil is then indexed to the next section. Further indexing brings coil 46 to the cutting station 58 for severance of the tubing into individual coils, by which stage the applied solvent has dried to the extent necessary to form the weak bond beteween individual turns of the coil of tubing 46 to form a bonded coil 46', which is ejected from the coil winding apparatus 51 by automatic retraction of the mandrel 56, after which the coil 46' drops into bin 59. Thereafter, mandrel 56 returns to its extended position for receiving tubing thereon and forming another coil 46. Details of the coil winding apparatus 51 are in accordance with those of conventional wire winding machines having a multiple-station construction.

Further details of the preferred dispensing syringe 22 are shown in FIGS. 8 and 9. Dispensing syringe is of a generally conventional construction having been modified to include a coupler 61 that has a bore 62 for receiving the movable pivot shaft 39 (FIG. 1). The dispensing syringe 22, in order to handle solvents for tubing material, should be of a structure that is resistant to the particular solvent being used, typically such a structure including a metal valve, the various other portions being of teflon, glass and/or metal. Plunger 47 is spring-loaded by means of spring 63 or the like which rests along internal stop 64, the plunger 47 extending into barrel 65 for passage of fluid through a two-way check valve 66 and out of a dispensing tip 67.

Further details of the double check valve 66 are shown in FIG. 9, it being important that the valve used be extremely resistant to the development of air bubbles or bubbles of solvent vapor, since the presence of fluids within the barrel 65 of the dispensing syringe 22 other than the solvent being dispensed would be detrimental to the simultaneous and synchronized tracking and dispensing functions accomplished by the present invention. For example, if air or solvent vapor were to become entrapped within barrel 65, sponginess in the operation of the apparatus would develop, and the dispensing function would lag behind the tracking function, thereby throwing off the inherent uniformity of the amount of solvent delivered to each turn of the coil of tubing 46.

Two-way check valve 66 of the type illustrated in FIG. 9 includes conical valve means to minimize sticking within the valve 66 which could create a reduced pressure within the dispenser 22 and thus vaporize some of the solvent. More particularly, the preferred structure of valve 66 includes an intake valve portion 68 and a dispensing valve portion 69. When plunger 47 is depressed, the pressure of the liquid within the barrel 65 pushes on the dispensing check cone 71 to force it against the bias of the spring 72, while simultaneously pushing upon the intake check cone 73 in order to close the intake valve portion 68, whereupon the liquid passes through the dispensing valve portion 69 and out of the dispensing tip 67. In the preferred embodiment, this operation of the valve 66 takes place as the axis C moves from point C' to point C"; movement from point C" to point C' releases or pulls on the plunger 47, creating a lowered pressure situation with the barrel 65, at which time the dispensing check cone 71 returns to its seat 74, while intake check cone 73 is readily pulled away from its seat 75 without vaporizing the liquid to permit liquid to flow into the syringe barrel 65 from the reservoir 43.

FIGS. 10 and 11 illustrate the improved dispensing and tracking pattern achieved by this invention. FIG. 10 illustrates a solvent spraying technique not in accordance with this invention, the solvent being sprayed from a generally stationary nozzle 76, which, in addition to causing splashing and waste by spraying more solvent than is necessary, also results in the formation of a solvent pattern that is not uniform across the coil of tubing 46", the pattern being generally oval as illustrated. The tracking and dispensing operation in accordance with this invention as illustrated in FIG. 11 shows the development of the narrow path or locus of squirted solvent that is aimed directly at each turn and the spacing between turns of the coil 46. A minimal amount of solvent, approximating a line that is an arc of a large radius is dispensed, as opposed to the wide and broadening spray pattern illustrated in FIG. 10.

The alternative embodiment depicted in FIG. 12 is somewhat more difficult to adjust and tends to be less precise than the preferred embodiment, this tracking and dispensing mechanism being generally illustrated by reference numeral 121 to include a dispensing means 122 pivotally mounted to a base 123 along a stationary axis AA, a rigid arm 124 being pivotally mounted to a rotating means 125 along movable axis CC. Tracking and dispensing functions are accomplished simultaneously and in synchronization as the rotating means 125 is extended and collapsed, the tracking being along a coil of tubing 146.

In proceeding with the method according to this invention and in producing the product according to this invention, coils of tubing having individual turns thereof weakly bonded to each other, the length of tubing is wound around a mandrel to form a cylinder of tubing, such tubing usually being very flexible and resilient, such as polyvinylchloride tubing of the type utilized in medical equipment and medical devices, especially disposable medical devices.

A predetermined quantity of liquid, the liquid most advantageously being a very good solvent for the particular tubing material, for example tetrahydrofuran which is an especially fast and quick-drying solvent for polyvinylchloride, is dispensed in a fine stream through a narrow orifice simultaneously and in synchronization with tracking of the narrow orifice along the coil of tubing, the tracking itself being generally parallel to the height of the cylinder of tubing, and the flow of the solvent being a substantially uninterrupted stream or squirt, preferably generally perpendicular to a tangental plane of the coil, the stream being in the nature of a point of solvent that is tracked along a surface of the coil in a gradual arc. The stream thus dispensed is generated by applying mechanical pressure to a supply of solvent whereby the solvent is passed through the narrow orifice.

Once the narrow path of solvent is dispensed and tracked, the total amount thereof is so minute, on the order of 0.1 cc. of solvent, that the solvent passes by general capillary action along and between the adjacent windings of tubing in order to promptly dissolve surfaces of the tubing, which surfaces, upon rapid drying of the solvent, adhere to each other with a relatively weak bond along those portions thereof to which the solvent spread by way of capillary action.

The coils thus prepared can be readily and safely stored without danger of crimping or tangling during storage, they being in a form in which they can be readily uncoiled by pulling apart the free ends thereof, the uncoiling being accomplished without danger of knotting or tangling. Preferably, the tubing coils, when initially wound, have spacing therebetween, and the spacing is eliminated by pushing the coil windings until they are adjacent to each other, it being preferred that this pushing step be accomplished prior to the dispensing directly onto the underlying mandrel and in order to maximize capillary action by the closeness of the individual turns, although carrying out the pushing step after the dispensing and tracking operation is also quite acceptable.

When operating on an apparatus such as that illustrated in FIG. 7 herein, and when using tetrahydrofuran as the liquid or solvent for making a polyvinylchloride coil of approximately 10 turns, the apparatus produces a completed coil every 5 seconds, and only about 1 quart of tetrahydrofuran is used for a full day's production, a total of only about 0.1 cc of tetrahydrofuran being dispensed onto each coil, this amount being substantially fully dried within about 15 seconds, which is before the coil is indexed to the cutting station of the apparatus, all of this being accomplished without a timer as such or any other control mechanism for synchronizing the dispensing and tracking operations.

It will be apparent to those skilled in this art that the present invention can be embodied in various forms. Accordingly, this invention is to be construed and limited only by the scope of the appended claims.

I claim:

1. An apparatus for manufacturing coiled tubing having adjacent turns thereof detachably adhered together, comprising:

means for supplying a length of tubing would about an axis into a generally cylindrical coil of tubing having individual turns positioned generally adjacent to each other, said individual turns being detached from each other along their adjacent sides;

means for automatic silmultaneous tracking and dispensing of a solvent stream onto said generally cylindrical coil of tubing, the tracking means of said tracking and dispensing means having a narrow orifice that traverses said coil of tubing generally along a path connecting adjacent turns of said coil of tubing, the dispensing means of said tracking and dispensing means being pivotally mounted, the dispensing means providing a substantially uninterrupted narrow stream of said solvent through said narrow orifice while said tracking means is in operation, said dispensing means including a supply of said solvent and mechanical means for applying mechanical pressure to said supply of solvent to pass said solvent through said narrow orifice;

said tracking and dispensing means including mechanical means for applying said mechanical pressure to said dispensing means while automatically synchronizing said tracking of said narrow orifice along said coil of tubing, whereby a narrow stream of solvent dissolves at least a portion of the adjacent sides of the individual turns of the coil and detachably adheres together said portions of the adjacent sides, said solvent being applied in an amount that is uniform per turn of tubing.

2. The apparatus of claim 1, wherein said pivotally mounted dispensing means includes a syringe having said narrow orifice.

3. The apparatus of claim 1, wherein said tracking and dispensing means includes: a base; a dispensing syringe having a dispensing end including said narrow orifice and an opposite end, said dispensing syringe being pivotally mounted to said base along a first axis that is generally transverse to said dispensing syringe at a location along the line defined by said dispensing end and said opposite end; a rigid arm having one end and an opposite end, said rigid arm being pivotally mounted at its said one end to said base along a second axis that is generally parallel to and offset a preselected distance from said first axis, said opposite end of the rigid arm being pivotally mounted along a third axis that is generally parallel to and movable with respect to said first and second axes; said opposite end of the dispensing syringe being in operative interengagement with said rigid arm; and a rotation effecting means for rotating said dispensing syringe and said rigid arm about said axes.

4. The apparatus of claim 1, wherein said tracking and dispensing means includes: a base; a dispensing means having a dispensing end including said narrow orifice and an opposite end, said dispensing means being pivotally mounted to said base along a first axis that is generally transverse to said dispensing means at a location along the line defined by said dispensing end and said opposite end; a rigid arm having one end and an opposite end, said rigid arm being pivotally mounted, at its said one end to said base along a second axis that is generally parallel to and offset a preselected distance from said first axis, said opposite end of the rigid arm and said opposite end of the dispensing means each being pivotally mounted along a third axis that is generally parallel to and that is movable relative to said first and second axes; and a rotation effecting means for rotating said dispensing means about said first and third axes and said rigid arm about said second and third axes.

5. The apparatus of claim 1, wherein said tracking and dispensing means includes: a base; a dispensing syringe having a dispensing end including said narrow orifice and an opposite end, said dispensing syringe being pivotally mounted to said base along a first axis that is generally transverse to said dispensing syringe at a location along the line defined by said dispensing end and said opposite end of the dispensing syringe; a rigid arm having one end and an opposite end, said rigid arm being pivotally mounted at its said one end to said base along a second axis that is generally parallel to and offset a preselected distance from said first axis; a rotation effecting means, said rotation effecting means being a telescoping arm having one end mounted to said base and an opposite end; and said opposite end of the rigid arm, said opposite end of the telescoping arm and said opposite end of the dispensing syringe each are pivotally mounted along a third axis that is generally parallel to and that is movable relative to said first and second axes.

6. The apparatus of claim 1, wherein said tracking and dispensing means includes: a base; a dispensing syringe having a dispensing end including said narrow orifice and an opposite end, said dispensing syringe being pivotally mounted to said base along a first axis that is generally transverse to said dispensing syringe, said first axis passing through said dispensing syringe at a location between said dispensing end and said opposite end; a rigid arm having one end and an opposite end, said rigid arm being pivotally mounted, at its said one end, to said base along a second axis that is generally parallel to and offset a preselected distance from said first axis; a telescoping arm having one end mounted to said base and an opposite end, said opposite end of the rigid arm and said opposite end of the telescoping arm both being pivotally mounted along a third axis that is generally parallel to and movable with respect to said first and second axes; said rigid arm having an extension member rigidly projecting beyond said one end of the rigid arm, said extension member being pivotally mounted to said opposite end of the dispensing syringe; and the opposite end of the dispensing syringe being in operative interengagement, through said rigid arm, with said opposite end of the telescoping arm.

7. The apparatus of claim 3, wherein said preselected distance that the first axis is offset from the second axis is selected by an adjustment means for varying the extent that said completely mechanical means applies pressure to said dispensing syringe and for varying the length of said tracking of the narrow orifice.

8. The apparatus of claim 3, wherein said pivotal mounting of the rigid arm includes a ball joint.

9. The apparatus of claim 3, wherein said rigid arm is a telescoping strut having a preload force being above forces developed during operation of the tracking and dispensing means and being below forces capable of being applied by human hands.

10. The apparatus of claim 1, wherein said means for supplying a length of tubing is a winding apparatus having a plurality of stations and a plurality of mandrels that are indexed from station to station, said apparatus including a winding station at which the length of tubing is wound, a pusher at one station for sliding together said coil of tubing to a predetermined coil length, said tracking and dispensing means at one station, and a coil cutting mechanism at another station.

11. The apparatus of claim 1, wherein said narrow orifice is included on a pivotally mounted dispensing syringe having a plunger communicating with a barrel having said supply of solvent, and a two-way check valve between said barrel and said narrow orifice, said check valve being in solvent passing, air tight communication with a solvent reservoir.

12. A method for manufacturing coiled tubing having adjacent turns thereof detachably adhered together, comprising:

winding a length of tubing about an axis to form a generally cylindrical coil of tubing having individual turns positioned generally adjacent to each other, said individual turns being detached from each other along their adjacent sides;

automatically and simultaneously tracking and dispensing a narrow stream of solvent onto the coil of tubing generally along a path connecting adjacent turns of said coil of tubing, said dispensing providing a substantially uninterrupted narrow stream of said solvent while said tracking is proceeding, said tracking and dispensing having an automatic synchronizing feature whereby the dispensing step and the tracking step are carried out by mechanical means for applying pressure to dispense solvent while simultaneously moving said narrow stream of solvent through said tracking path, whereby said solvent is applied in an amount that is uniform per turn of tubing, said automatic synchronization of the tracking and dispensing steps including providing a plurality of rotation points operatively interconnected with each other; and permitting the path of solvent to spread by capillary action to a portion of the adjacent sides of the individual turns of the coil and to dry thereat in order to detachably adhere together said portions of the adjacent sides.

13. The method of claim 12, wherein said tracking and dispensing step directs the narrow stream of solvent in a direction generally perpendicular to a tangental plane of the coil of tubing.

14. The method of claim 12, wherein said tracking step directs the narrow stream of solvent in a path, approximating a locus of points along a gradual arc.

15. The method of claim 12, wherein said step of providing a plurality of rotation points for said automatic synchronization of the tracking and dispensing steps includes providing a stationary first rotation point and a stationary second rotation point offset from each other by a preselected distance, providing a movable third rotation point spaced from and operatively interconnected with said first and second rotation points such that movement of said movable third rotation point carries out said dispensing and tracking in a simultaneous and synchronized manner.

16. The method of claim 12, wherein said step of providing a plurality of rotation points for said automatic synchronization of the tracking and dispensing steps includes providing a stationary first rotation point and a stationary second rotation point offset from each other by a preselected distance, providing a movable third rotation point spaced from and operatively interconnected with said first and second rotation points, and moving said third rotation point to carry out said tracking step while maintaining a constant distance between the second rotation point and the third rotation point and while reducing the distance between the first rotation point and the third rotation point to accomplish said dispensing step.

17. The method of claim 12, wherein said winding step spaces apart the individual turns and said winding step is followed by sliding together said spaced turns until a predetermined coil length is attained.

18. The method of claim 12, wherein said tubing is polyvinylchloride tubing, said solvent is tetrahydrofuran, and said narrow stream of solvent is generated by a dispensing syringe having a narrow orifice.

19. A coiled tubing product having adjacent turns thereof detachably adhered together, made by the process comprising:

winding a length of flexible and stretchable tubing about an axis to form a generally cylindrical coil of tubing having individual turns positioned generally adjacent to each other, said individual turns being detached from each other along their adjacent sides;

automatically and simultaneously tracking and dispensing a narrow stream of solvent onto the coil of tubing generally along a path connecting adjacent turns of said coil of tubing, said dispensing providing a substantially uninterrupted narrow stream of said solvent while said tracking is proceeding, said tracking and dispensing having an automatic synchronizing feature whereby the dispensing step and the tracking step are carried out by a single mechanical means for applying pressure to dispense solvent while simultaneously moving said narrow stream of solvent through said tracking path, whereby said solvent is applied in an amount that is uniform per turn of tubing, said automatic synchronization of the tracking and dispensing steps including providing a plurality of rotation points operatively interconnected with each other; and permitting the path of solvent to spread by capillary action to a portion of the adjacent sides of the individual turns of the coil and to dry thereat in order to detachably adhere together said portions of the adjacent sides, said individual turns of the product being detached from each other along their said adjacent sides except that said product individual turns are detachably adhered to each other at said portions of their said adjacent sides, said detachably adhered portions having been formed by solvent spread through capillary action between the individual turns of the flexible and stretchable tubing.

20. The product of claim 19, wherein said tubing is made of polyvinylchloride and said solvent is tetrahydrofuran.

21. The product of claim 19, wherein said step of providing a plurality of rotation points for said automatic synchronization of the tracking and dispensing steps includes providing a stationary first rotation point and a stationary second rotation point offset from each other by a preselected distance, providing a movable third rotation point spaced from and operatively interconnected with said first and second rotation points, and moving said third rotation point to carry out said tracking step while maintaining a constant distance between the second rotation point and the third rotation point and while reducing the distance between the first rotation point to accomplish said dispensing step.

* * * * *